US00PP28435P3

(12) United States Plant Patent
Byrne et al.

(10) Patent No.: US PP28,435 P3
(45) Date of Patent: Sep. 26, 2017

(54) NECTARINE TREE NAMED 'SMOOTH ZEST TWO'

(50) Latin Name: *Prunus persica*
Varietal Denomination: Smooth Zest Two

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 40 days.

(21) Appl. No.: 14/544,501

(22) Filed: Jan. 13, 2015

(65) Prior Publication Data

US 2016/0205826 P1 Jul. 14, 2016

(51) Int. Cl.
*A01H 5/08* (2006.01)

(52) U.S. Cl.
USPC ..... Plt./19

(58) Field of Classification Search
USPC ..... Plt./190
See application file for complete search history.

(56) References Cited

PUBLICATIONS

Philips, 2013. AgriLife Today.*
The Brooks and Olmo Register of Fruit and Nut Varieties, 3rd Ed., American Society of Horticultural Science Press, Alexandria, VA, 1997.
Byrne et al.; 'TexFirst', An early ripening low chill peach for the subtropics; HortScience; 2012; pp. 1803-1804; vol. 47.
Andrews et al.; 'FlordaKing' peach; HortScience; 1979; pp. 81-82; vol. 14.
Byrne et al.; 'TexKing', an Early Ripening, Medium-chill Peach; HortScience; Apr. 2004; pp. 442-443; vol. 39.
Sherman et al.; 'Sunraycer' Nectarine; HortScience; 1995; p. 154; vol. 30(1).

* cited by examiner

*Primary Examiner* — Keith Robinson
(74) *Attorney, Agent, or Firm* — Ramey & Schwaller, LLP

(57) ABSTRACT

Disclosed is a new variety of *Prunus persica* named 'Smooth Zest Two'. This new variety, which requires 200 to 250 chilling units of dormancy, is considered to be a nectarine tree of early season maturity, which ripens in early to mid May in the medium chill zone of Texas and produces yellow fleshed fruit that are very firm, attractively colored, and suitable for both the local and regional fresh fruit market.

4 Drawing Sheets

BACKGROUND OF THE INVENTION

Field of the Invention

This invention relates to a nectarine tree referred to as a variety of *Prunus persica* named 'Smooth Zest Two'. 'Smooth Zest Two', which requires 200-250 chilling units of dormancy, produces a high quality, firm clingstone nectarine that matures early in the season.

SUMMARY OF THE INVENTION

'Smooth Zest Two' is being released for use in the low to medium chill zones where cultivars such as 'TexFirst' (U.S. Plant Pat. No. 26,119), 'Flordaking' (not patented, Andrews et al., 1979), 'Texking' (U.S. Plant Pat. No. 14,627), and 'Sunraycer' (not patented, Sherman et al. 1995) are adapted. 'Smooth Zest Two' bears crops of clingstone, melting flesh nectarines in early to mid May in the low to medium chill zones of Texas. This new nectarine fruits well in low chill zones that receive 200-250 chilling units.

Origin of the Variety

The present nectarine tree was the result of an ongoing Stone Fruit Breeding Program of Texas A & M University, College Station, Brazos County, Tex. To this end, both controlled crosses are made each year to produce seedling populations from which improved progenies are evaluated and selected.

'Smooth Zest Two' (TX2B261N) [*Prunus persica* (Batsch) L.] originated in the Stone Fruit Breeding Program, Department of Horticultural Sciences, Texas A&M University, located in College Station, Tex. 'Smooth Zest Two' was selected from a cross between two unreleased nectarine selections: TX1B38N (not patented) and TX95128N (not patented). TX1B38N, the female parent, is an open pollinated seedling from 'Sunraycer' (not patented, Sherman et al., 1995) and TX95128N, the male parent, is a nectarine of unknown parentage derived from the Florida nectarine germplasm. The seedlings from this cross were planted in a high density selection orchard in 2002 and the selection TX1B261N was chosen as having superior fruit size and quality in 2004.

Two-year and older trees of the selections were subsequently evaluated during the 2006 through 2010 fruit growing seasons in three locations: two medium chill sites (Floresville and College Station, Tex.) and a higher chill location (Fowler, Calif.).

Asexual Reproduction of the Variety

'Smooth Zest Two' was bud grafted onto virus-free Nemaguard (not patented, Brooks and Olmo, 1997) peach rootstock in June 2004 at the nursery site in Oakdale, Calif. The variety was subsequently planted at the experimental orchard in the central portion of the San Joaquin Valley, near Fowler, Fresno County, Calif. and in two sites in Texas (College Station and Floresville). Fruit from the resulting propagation has been evaluated during the period from 2006 to 2010 fruit seasons. This evaluation clearly demonstrated that the re-propagated trees were true to the characteristics of the original seedling in all observable aspects.

BRIEF DESCRIPTION OF THE DRAWINGS

This new variety of nectarine tree is illustrated by the accompanying photographs. The flowers, fruit, and shoots in the pictures were obtained from a tree that was five-years old.

BOTANICAL DESCRIPTION OF THE VARIETY

Figure 1:
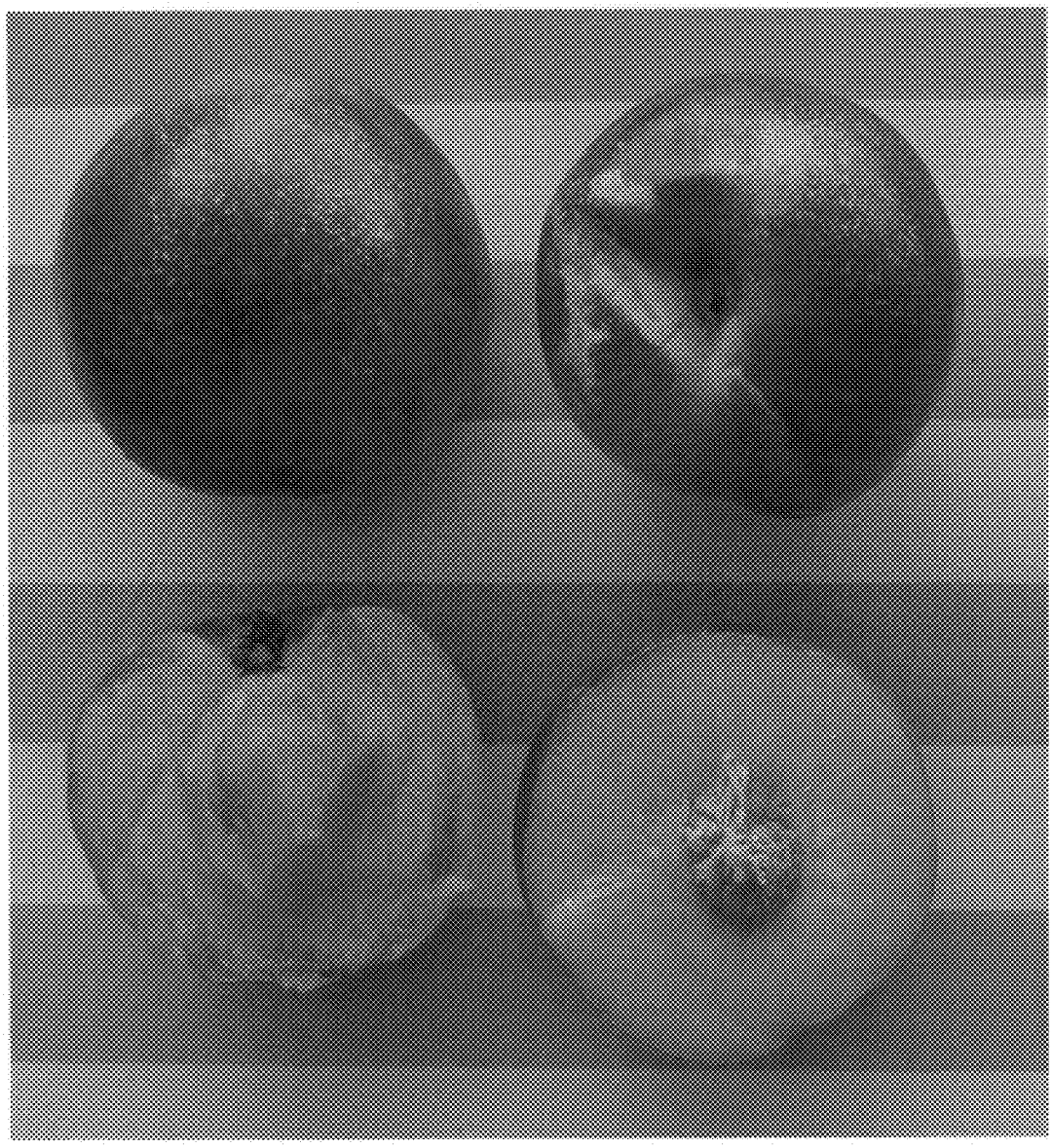
FIG. 1. Fruit of 'Smooth Zest Two' showing apical and distal views as well as fruit dissected in the axial plane to illustrate the flesh and stone characteristics.
Figure 2:
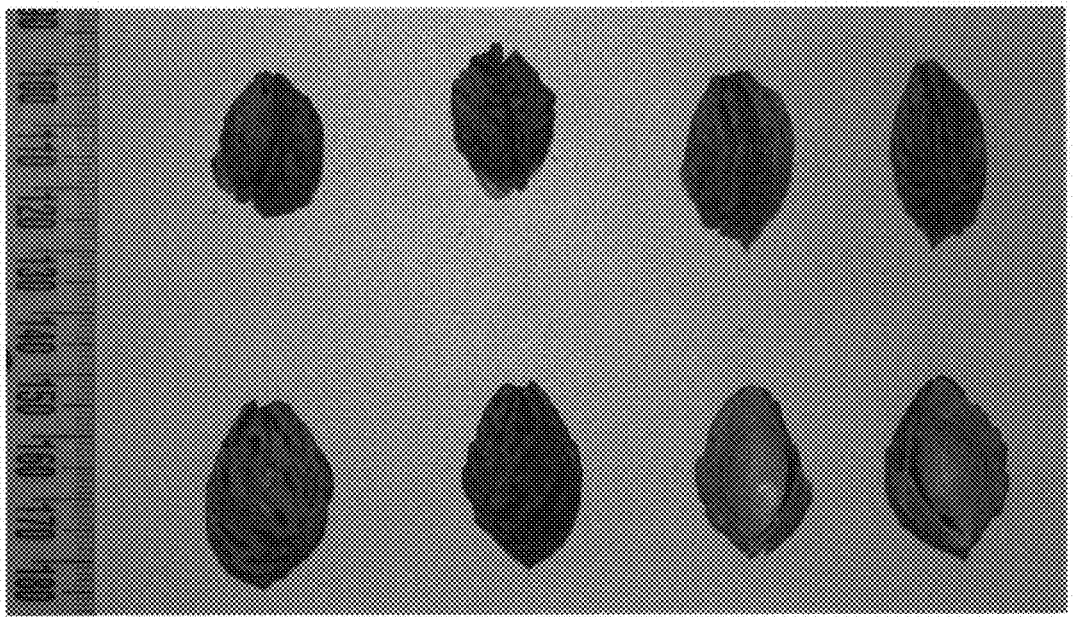
FIG. 2. Dried endocarps of 'Smooth Zest Two' showing the size, shape and texture. The ruler is demarcated in millimeters.
Figure 3:
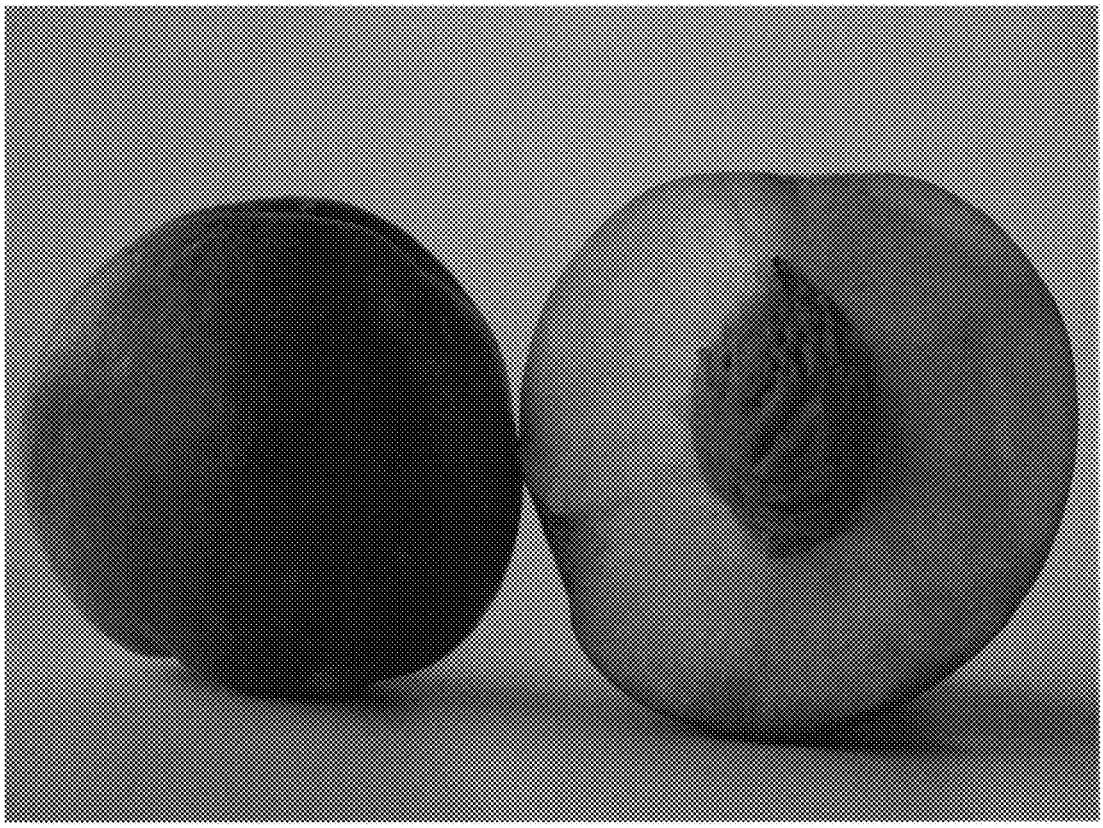
FIG. 3. 'Smooth Zest Two' nectarine showing the external and internal color of the fruit and endocarp.
Figure 4:
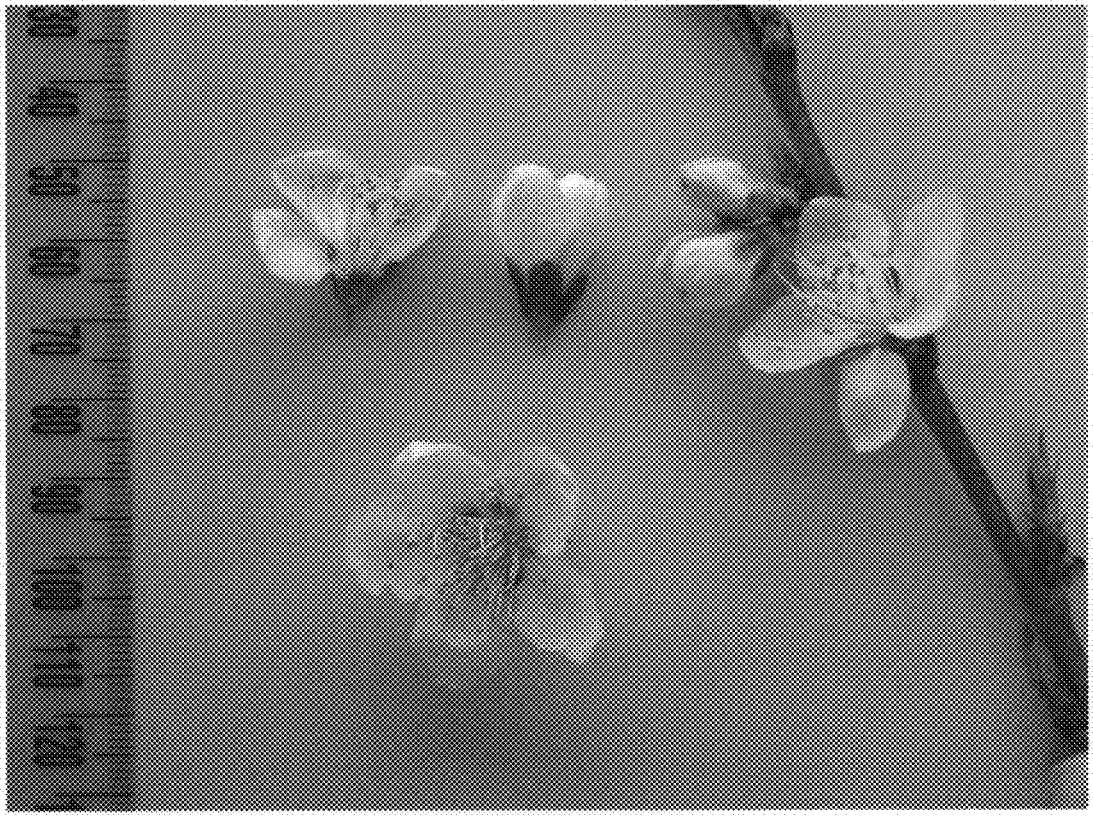
FIG. 4. The showy flowers of 'Smooth Zest Two'. The ruler is in millimeters.

Referring more specifically to the pomological details of this new and distinct variety of nectarine tree, the following has been observed under the ecological conditions prevailing at the experimental orchards in the medium chill zones of Texas. All major color code designations are by reference to The R.H.S. Colour Chart (2001; 2005) provided by The Royal Horticultural Society of Great Britain. Colors are approximate as color depends on horticultural practices such as light level and fertilization rate, among others. The trees observed were five-years old.

Tree

Size: Generally average to above average as compared to other common peach and nectarine cultivars ripening in the early season of maturity.

Height: 3.5 m at the end of the 2012 growing season (five-years old).

Width: 3 m at the end of the 2012 growing season (five-years old).

Vigor: High.

Density: Medium to high.

Productivity: Productive.

Shape: The 'Smooth Zest Two' exhibits a generally spreading growth habit typical of commercial varieties of nectarine such as 'TexKing' (U.S. Plant Pat. No. 14,627) and 'TexRoyal' (not patented, Byrne and Bacon, 1991).

Current season growth: The current season growth for the new variety was approximately 37 to 43 inches (0.94-0.96 m).

Regularity of bearing: Regular, and considered hardy under typical conditions found in the low to medium chill zones of Texas and in the central San Joaquin Valley, Calif.

Trunk

Size: Approximately 3.5 inches (8.9 cm) in diameter and 12 inches (30.5 cm) in circumference when measured at a distance of approximately 12 inches (30.5 cm) above the soil level, at the end of the 2012 growing season on a five-year old tree.

Bark texture: Considered moderately rough with numerous folds of papery scarf-like skin being present.

Bark coloration: Variable, colors present are 189C-D of the Greyed-Green Group, 200B-D of the Brown Group and 201C-D of the Grey Group.

Branches

Size: Considered medium small to medium for the variety.

Thickness and length: Medium small to medium (about 2.2 cm in diameter as measured 10 cm from the trunk on a five-year old tree) as compared to other varieties. The length of the branches are limited by pruning to a 3 to 5 foot (approximately 0.9 to 1.5 m) length depending on the position in the tree.

Surface texture: Average and appearing furrowed on wood that is several years old.

Lenticels: Numerous flat, oval lenticels present. The lenticels range in size from approximately 3 to 7 mm in width and were approximately 1 mm in height.

Current season shoots:

*Surface texture*.—Substantially glabrous.

Internode length: Approximately 10 to 13 mm as measured in the middle of a current season stem.

Color of mature branches: The predominant colors are 166A and 174A of the Greyed-Orange Group.

Current season shoots:

*Color*.—Green (144A of the Yellow-Green Group) with a reddish brown coloration on the exposed surfaces (166A of the Greyed-Orange Group and 179A and 181A of the Greyed-Red Group). The upper exposed surface of current season growth exhibits a medium intensity of anthocyanins.

Leaves

Size: Considered moderately large for the species. Leaf measurements have been taken from vigorous upright current season growth approximately at mid-shoot.

Leaf length: Approximately 150 to 182 mm.

Leaf width: Approximately 41 to 47 mm.

Leaf thickness: Less than 1 mm.

Leaf form: Lanceolate and occasionally wavy and crinkled.

Leaf tip form: Acuminate.

Leaf upper surface color: Green varying among 137A-B of the Green Group and 146A-B of the Yellow-Green Group.

Leaf lower surface color: Green varying among 146A-D of the Yellow-Green Group.

Leaf mid-vein color: Light yellow green (150D and 154D of the Yellow-Green Group).

Leaf margins:

*Form*.—Considered crenulate.

*Uniformity*.—Considered generally uniform.

Leaf petioles:

*Size*.—Considered medium.

*Length*.—Approximately 11-12 mm.

*Thickness*.—Approximately 2 mm.

*Color*.—Light yellow green (150D and 154D of the Yellow-Green Group).

Leaf glands:

*Size*.—Approximately 1 mm in height and less than 1 mm in width.

*Number*.—Generally 3-4 per leaf.

*Type*.—Globose.

*Color*.—Brown (199A of the Grey-Brown Group).

Leaf stipules: Early deciduous.

*Size*.—Length — Approximately 8-9 mm. Width — Less than 1 mm.

*Form*.—Lanceolate.

*Color*.—Light green (Yellow-Green Groups N144A-C and 151A-C), with red (Orange-Red Group N34A, Red Groups 46A-B and 53A-B).

*Ratio of wood (leaf) buds to flowering buds*.—1 to 2 flower buds per vegetative bud.

Flowers

Floral buds:

*General*.—The floral buds are considered to be medium to medium large in size, conic in form, and slightly appressed relative to the bearing shoot.

*Color*.—The bud scales are gray-brown (approximately Greyed-Purple Group 183C-D). The buds are considered hardy under the typical climatic conditions in the low and medium chill zones of Texas and in central San Joaquin Valley, Calif. climatic conditions.

*Length and width*.—Approximately 5 to 10 mm in length and 3 to 5 mm in width.

*Blooming type*.—Considered quite early in relation to other peach cultivars commonly growing in the low to medium chill zone of Texas. Date of full bloom was between February 1st and February 10th during the period between 2008 and 2012 with an average full bloom date of February 5th, 12-14 days before 'Flordaking' and 'Texking'.

*Flower type*.—Showy.

*Flower size*.—Flower diameter at full bloom is approximately 32 to 40 mm. The length of the flower at the pink bud stage before opening varied from 15 to 21 mm depending on its stage of development.

*Bloom quantity*.—Considered abundant.

*Flower bud frequency*.—Normally 1 to 2 per node.

Petal Size:

*General*.—Considered medium large for the species.

*Width*.—Approximately 14 to 15 mm.

*Length*.—Approximately 17 mm.

Petal form: Broadly ovate.

Petal count: Nearly always 5.

Petal color: Light pink when young (Red-Purple Group 62D, 65C-D and 73D).

Petal claw:

*Form*.—The claw is considered truncate in shape and has a small to medium size when compared to other varieties.

*Length*.—Approximately 1 mm.

*Width*.—Approximately 1 mm or less.

Petal margins: Generally considered smooth.

Petal apex:

*Generally*.—The petal apices appear slightly domed.

Flower pedicel:

*Length*.—Considered present, and having an average length of approximately 2 to 3 mm.

*Thickness*.—Considered average, approximately 1 mm.

*Color*.—A light green (Yellow-Green Group N144D and 145A-B).

Floral nectaries:

*Color*.—Bright orange (Orange Group 25A-B and N25A-C).

Hypanthium:

*Surface texture*.—Generally glabrous.

*Color*.—A brownish red with light green (approximately Yellow-Green Group 145A-B, Greyed-Red Group 178A-B, 181A and 183A-C).

Sepals:

*Surface texture*.—The surface has a short, fine, and wooly texture.

*Size*.—Average, and ovate in form. The sepals range from approximately 5.0 to 6.7 mm in length and 3.3 to 5.0 mm in width.

*Color*.—A brownish red with green (approximately Yellow-Green Group 145A-B, Greyed-Red Group 178A-B, 181A and 183A-C).

Anthers:

*General*.—Average in size for the species. The anthers are approximately 1 mm in length and 0.5 mm in width.

*Color*.—Yellow (approximately Greyed-Orange Group 163B-C).

*Pollen production*.—Pollen is abundant, and is a yellow color (approximately Yellow Groups 5A-B and 12A-13B).

Filaments:

*Size*.—Variable in length, approximately 12 to 13 mm, with the filaments slightly shorter or equal to the pistil. The stamens are slightly below or equal with the pistil height and do not protrude when the flowers are at the pink bud stage of development.

*Color*.—White (approximately White Group N999D) (from R.H.S. Colour Chart, 2005).

Pistil:

*General*.—Average in size, but slightly longer or equal to the general anther height.

*Length*.—Approximately 15 to 17 mm, including the ovary.

*Color*.—Considered a very light yellow when young (approximately Green-Yellow Group 1C-D and Yellow Group 2C-D).

*Pubescence*.—Absent. The pistil including the ovary is not pubescent.

Fruit

Maturity when described: The present variety of fruit is described, as it would be found in its firm ripe condition at full commercial maturity in early to mid May in the medium chill zone of Texas. 'Smooth Zest Two' ripens 3-4 days after 'Flordaking' (not patented, Andrews et al., 1979) and with or 1-2 days before 'Smooth Delight One' (U.S. patent application Ser. No. 14/544,508) and 'Smooth Delight Two' (U.S. patent application Ser. No. 14/544,522) in the medium chill zone.

Size:

*General*.—Medium large for the season and considered uniform.

*Average cheek diameter*.—Approximately 63 to 74 mm.

*Average suture diameter*.—Approximately 65 to 76 mm.

*Average axial diameter*.—Approximately 65 to 69 mm.

Fruit form: Generally round to round-ovate in its lateral aspect. Occasionally the fruit exhibits less symmetry when comparing the suture height with the line opposite the suture. The fruit is generally uniform in symmetry when viewed from the apical aspect, but occasionally exhibits unequal halves.

Fruit suture: Generally, the suture appears as a thin line that extends from the base to the apex, and appears deeper at the apex, forming a shallow basin at the apical point. No apparent callusing or stitching exists along the suture line.

*Color*.—The suture normally is the same color as the underlying blush (42A-D, 45A-D, 26A-B, 47A-B and 53A-B of the Red Group).

*Ventral surface*.—Form — Considered uniform.

Stem cavity:

*Size*.—Considered medium for the species.

*Width*.—Approximately 22 to 30 mm.

*Length*.—Approximately 25 to 30 mm.

*Depth*.—Approximately 10 to 13 mm.

Fruit base: Generally considered truncate in form, and uniform.

Fruit apex: Generally considered depressed and usually recessed below the height of the apical shoulders.

Fruit stem:

*Generally*.—Considered medium in length, approximately 9 to 10 mm.

*Thickness*.—Approximately 2 to 3 mm.

*Color*.—Generally a light green (144B-D and 145B of the Yellow-Green Group).

Fruit skin: Generally considered medium or average in thickness.

*Surface texture*.—The variety has no pubescence.

*Skin acidity*.—Considered neutral.

*Tenacious to flesh*.—Yes at commercial maturity.

*Tendency to crack*.—Some cracking observed.

*Skin color*.—Generally — Variable, with a small (approximately 30%) to a large (approximately 70%) percentage of the fruit surface covered with an attractive blush as described below under Blush Color.

*Pubescence*.—Absent. The glabrous skin has a medium glossiness.

*Blush color*.—This blush ranges from medium to dark red (42A-D, 45A-D, 26A-B, 47A-B and 53A-B of the Red Group) with many degrees of shading and blending occurring between these colorations.

*Skin ground color*.—This is generally present in variable percentages covering approximately 35-50% of the fruit's surface. The skin ground color is yellow with a small amount of green present (1B-C of the Green-Yellow Group, 2C-D, 3D, 4C-D, 5C-D and 8B-C of the Yellow Group and 14C-D of the Yellow-Orange Group).

Flesh color: Generally considered variable from light to medium yellow (11C-D and 12D of the Yellow Group, 15C-D and 16B-D of the Yellow-Orange Group and 155A-D of the White Group).

Flesh texture: Generally, the flesh is considered firm at commercial maturity.

Ripening: Generally the fruit of the present variety ripens evenly.

Flavor: Considered sweet with slightly acidic flavor.

Aroma: Pleasant and reasonably abundant.

Eating: Generally considered very good, particularly for an early ripening variety.

Stone

Attachment: Clingstone (strongly adherent) at commercial maturity.

Stone size: Generally considered medium-small to medium relative to the ratio of stone to fruit size.

*Length*.—Approximately 27 to 29 mm.

*Width*.—Approximately 17 to 20 mm.

*Thickness*.—Approximately 14 to 16 mm.

Stone form: Generally the stone is considered elliptical.

Stone base angle: Considered narrow to medium.

Apex shape: The stone apex is narrow to medium.

Stone shape: The stone shape is generally elongated to very elongated.

Stone surface:

*Surface texture*.—Minor surface markings consists of line grooves, numerous single pits and pit grooves.

*Ridges*.—Numerous fine ridges are present basally, and converge towards the base of the stone.

*Ventral edge*.—Width — Considered small to medium and having a dimension of approximately 4 to 6 mm at the mid-suture.

*Dorsal edge*.—Shape — Grooved and having moderately rough edges.

*Stone color*.—The color of the dry stone is medium brown (approximately 164B and 165C-D of the Greyed-Orange Group and N199C-D of the Grey-Brown Group). The color of the inside surface of the endocarp is primarily 164B-C and 165C-D of the Greyed-Orange Group.

*Tendency to split*.—Some splitting observed.

*Kernel*.—The kernel fills the endocarp at harvest. When dried the shriveled kernels measure approximately 2-3 mm in thickness, 7-8 mm in width, and 14-15 mm in length. The colors of the shriveled kernels are variable, ranging from medium to dark brown (164A and 165A-B of the Greyed-Orange Group and N199C-D and 200D of the Greyed-Brown Group).

Use: The subject variety, 'Smooth Zest Two', is considered to be a nectarine tree of early-season maturity, which produces fruit which are firm, attractively colored, and which are useful for both local and regional fresh fruit markets.

Keeping quality: Good.

Resistance to insects and disease: No particular susceptibilities were noted or claimed.

Shipping quality: Average.

Although the new variety of nectarine tree possesses the described characteristics when grown under the ecological conditions prevailing in the low to medium chill zone of Texas, it will be understood that variations of the usual magnitude and characteristics incident to the changes in growing conditions, fertilization, pruning, and pest control are to be expected.

References

Andrews, C. P., W. B. Sherman, and P. M. Lyrene. 1979. 'Flordaking' peach. HortScience 14:81-82.

Anon. 2001. R.H.S. Colour Chart. The Royal Hort. Soc., London.

Brooks, R. M. and H. P. Olmo. 1997. Register of New Fruit and Nut Varieties. 3rd Edition. American Society of Horticultural Science Press, Alexandria, Va.

Byrne, D. H. and N. Anderson. 2013. TexFirst, an Early-ripening, low chill peach for the subtropics. HortScience 47(2):1803-1804. U.S. Plant Pat. No. 26,119.

Byrne, D. H and N. Anderson. Nectarine tree, Smooth Delight One. U.S. patent application Ser. No. 14/544,508.

Byrne, D. H and N. Anderson. Nectarine tree, Smooth Delight Two. U.S. patent application Ser. No. 14/544,522.

Byrne, D. H. and T. A. Bacon. 1991. 'TexRoyal', a medium chilling peach. HortScience 26(10):1338-1340.

Byrne, D. H. and T. A. Bacon. 2004. 'TexKing', an early ripening medium chill peach. HortScience 39: 442-443. U.S. Plant Pat. No. 14,627. Mar. 23, 2004.

Sherman, W. B., P. C. Andersen, and P. M. Lyrene. 1995. 'Sunraycer' nectarine. HortScience 30(1): 154.

We claim:

1. A new and distinct *Prunus persica* tree, substantially as illustrated and described herein.

* * * * *